United States Patent
Rowden et al.

[11] Patent Number: 5,840,077
[45] Date of Patent: *Nov. 24, 1998

[54] UTERINE MANIPULATING ASSEMBLY FOR LAPAROSCOPIC HYSTERECTOMY

[75] Inventors: Jimmy M. Rowden, Olathe, Kans.; John E. Heaton, Kansas City, Mo.; Charles H. Koh, Mequon, Wis.; Kerry L. Blair, Olathe, Kans.

[73] Assignee: Blairden Precision Instruments, Inc., Lenexa, Kans.

[ * ] Notice: The term of this patent shall not extend beyond the expiration date of Pat. No. 5,643,285.

[21] Appl. No.: 544,163

[22] Filed: Oct. 17, 1995

Related U.S. Application Data

[63] Continuation-in-part of Ser. No. 324,656, Oct. 18, 1994, Ser. No. 325,907, Oct. 19, 1994, Pat. No. 5,520,698.

[51] Int. Cl.$^6$ .................................................. A61B 17/42
[52] U.S. Cl. ............................................ 606/112; 606/193
[58] Field of Search ..................................... 606/119, 191, 606/192, 193, 108, 172, 198; 604/96, 97, 98, 116, 117

[56] References Cited

U.S. PATENT DOCUMENTS

| | | | |
|---|---|---|---|
| 3,769,983 | 11/1973 | Merav | 128/207.15 |
| 5,237,985 | 8/1993 | Hodgson et al. | 128/17 |
| 5,409,496 | 4/1995 | Rowden et al. | 606/119 |
| 5,431,662 | 7/1995 | Nicholas | 606/119 |
| 5,520,698 | 5/1996 | Koh | 606/119 |
| 5,540,700 | 7/1996 | Rowden et al. | 606/119 |
| 5,624,399 | 4/1997 | Ackerman | 606/119 |

*Primary Examiner*—Robert A. Hafer
*Assistant Examiner*—Benjamin K. Koo
*Attorney, Agent, or Firm*—Lathrop & Gage, L.C.

[57] ABSTRACT

A colpotomy assembly 10 is adapted for insertion into a vaginal cavity for use in female pelvic surgical procedures employing the inflation of an abdominal cavity with a gas to facilitate the accessability to and visibility of female pelvic organs. The assembly has a vaginal extender 20, a uterine manipulator 16 and a flexible occluder. The occluder being mounted on a shaft of the uterine manipulator such that it permits relative movement of the shaft 26 during use.

12 Claims, 10 Drawing Sheets

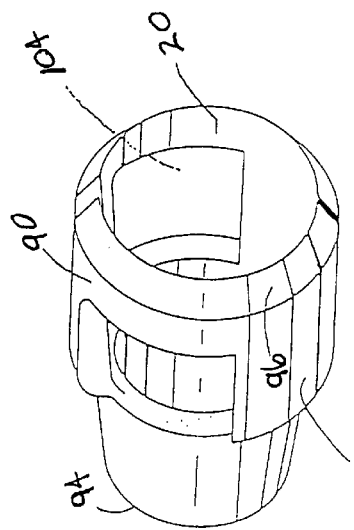
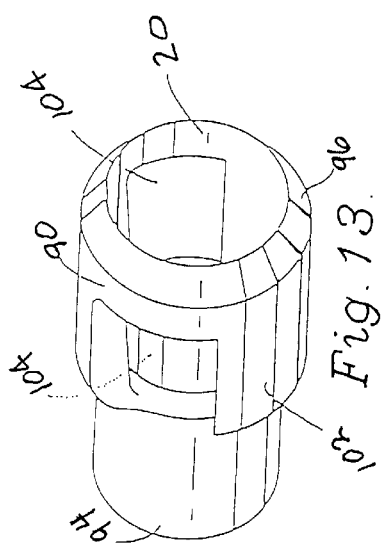
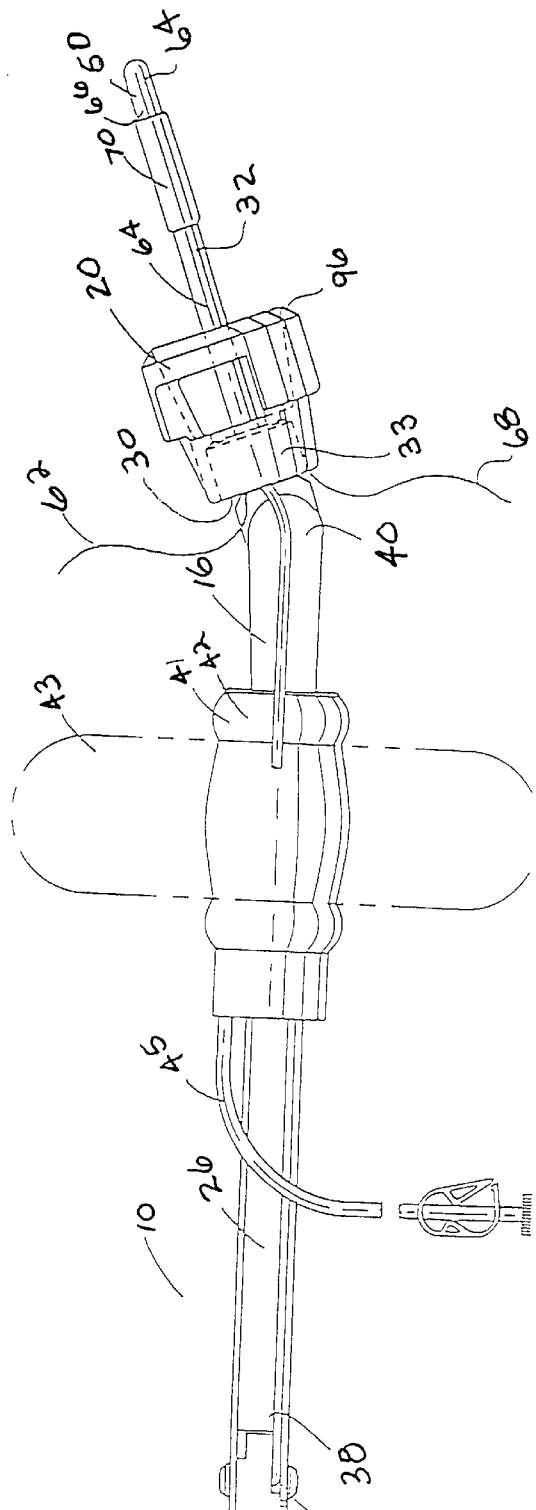
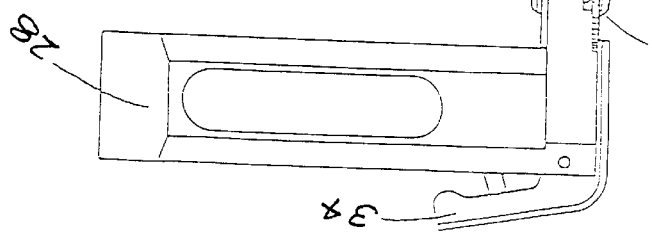

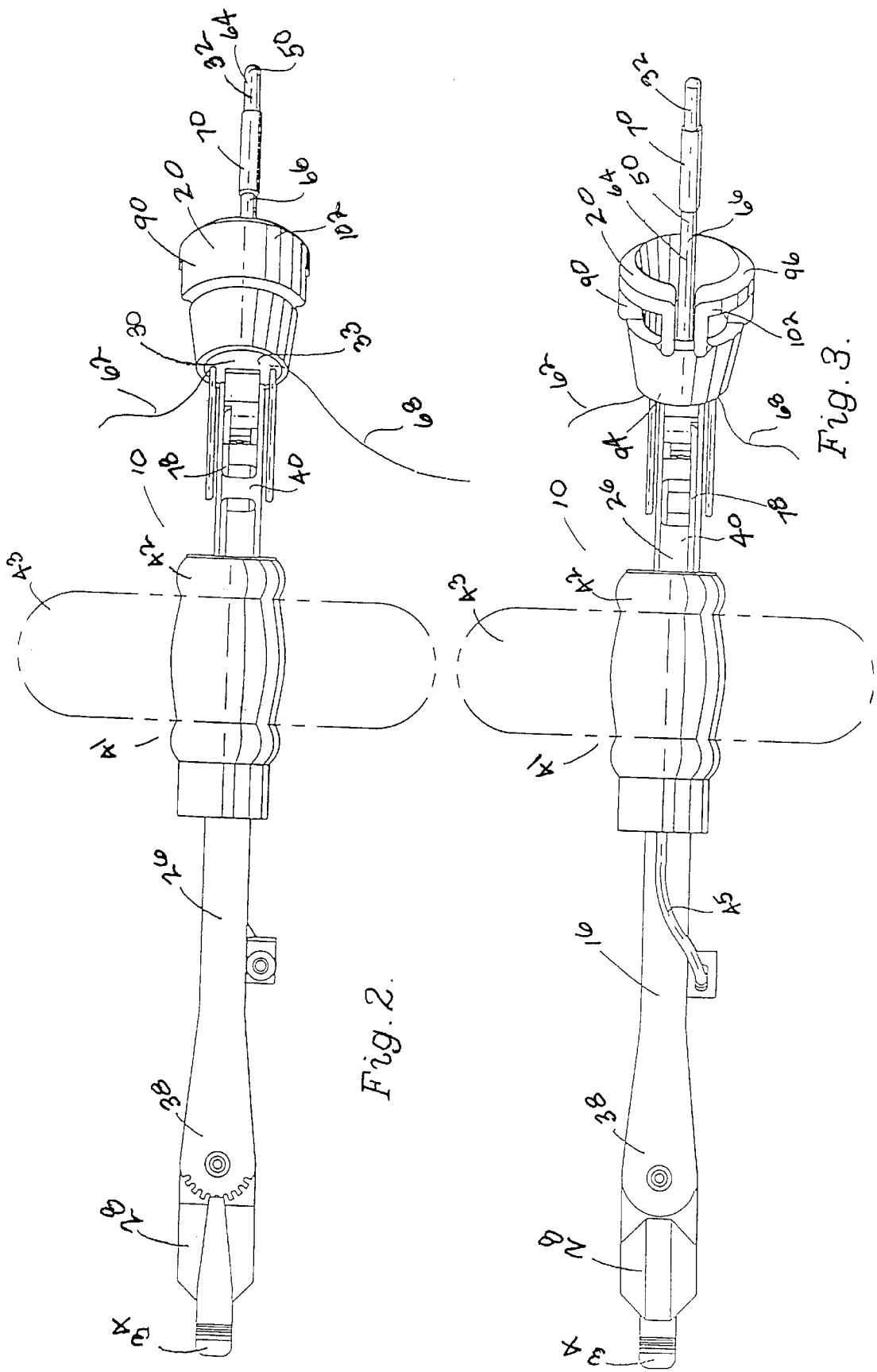

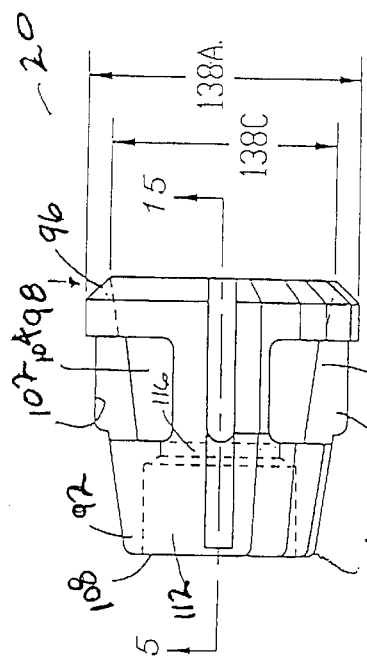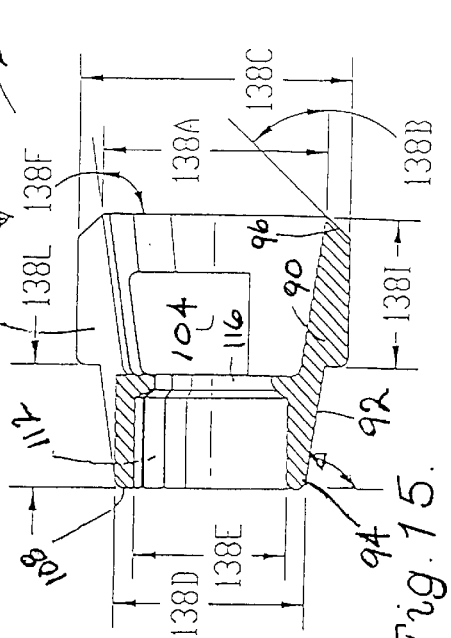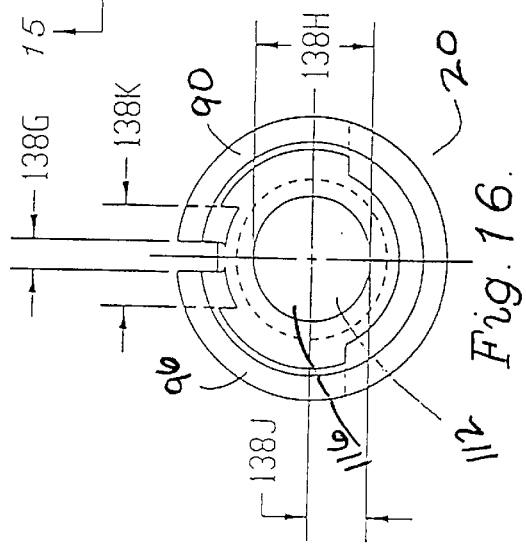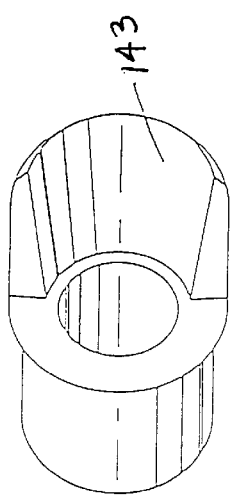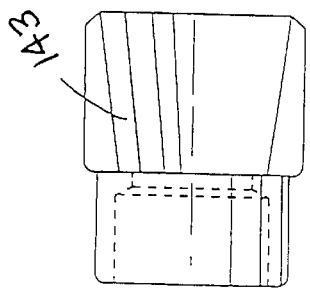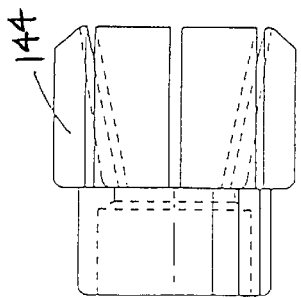

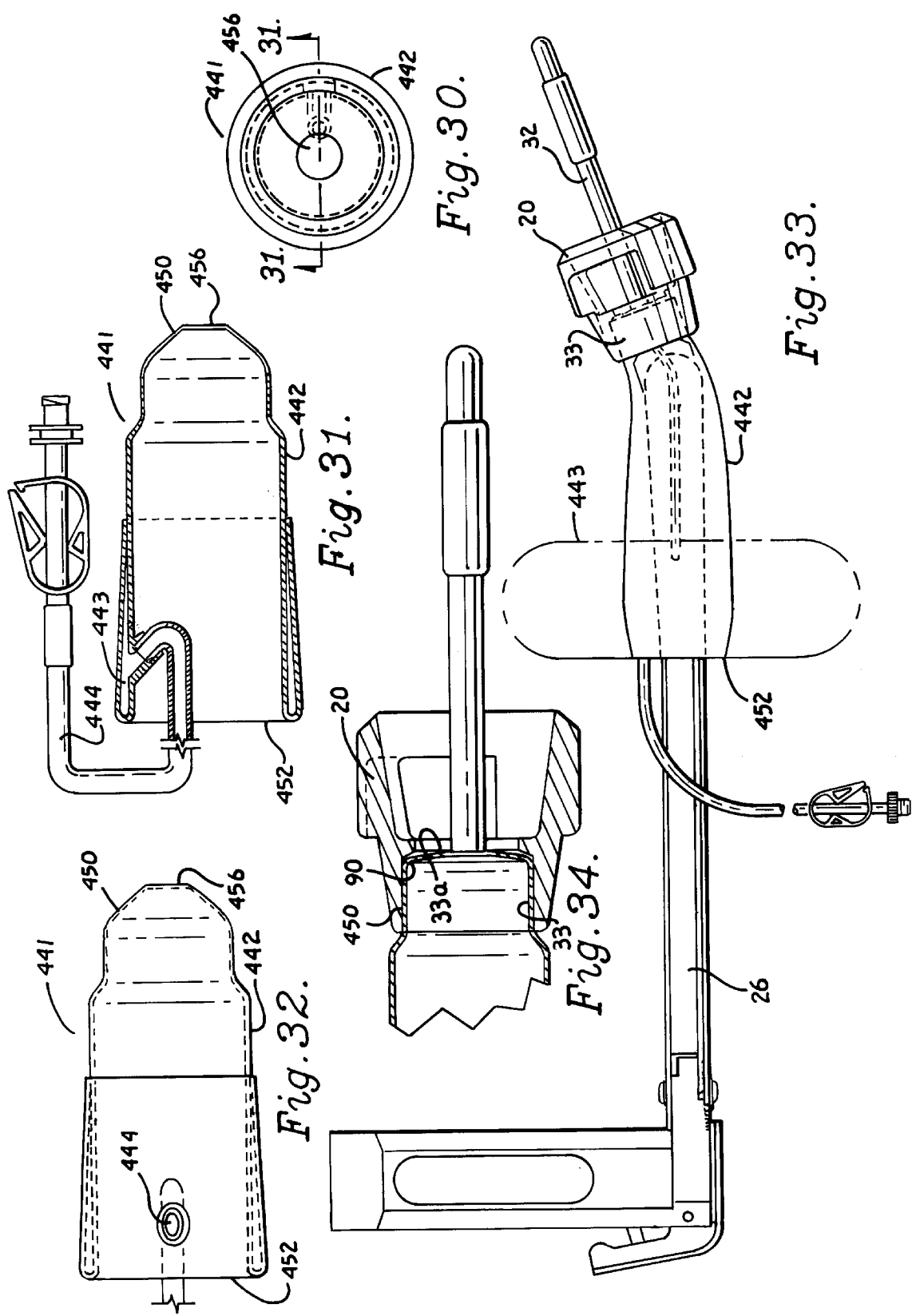

UTERINE MANIPULATING ASSEMBLY FOR LAPAROSCOPIC HYSTERECTOMY

RELATED APPLICATIONS

This is a continuation-in-part of application Ser. No. 08/324,656, filed Oct. 18, 1994, entitled Vaginal Extender for Colpotomy Surgery and Ser. No. 08/325,907, filed Oct. 19, 1994, now U.S. Pat. No. 5,520,698, entitled Simplified Total Laparoscopic Hysterectomy Method Employing Colpotomy Incisions. The teachings of application Ser. No. 08/324,656 and Ser. No. 08/325,907 are incorporated herein by reference.

BACKGROUND OF THE INVENTION

1. Field of the Invention

The present invention relates to a vaginal extender for use in performing various female pelvic surgeries, including laparoscopic hysterectomy, laparoscopically assisted vaginal hysterectomy, and other female pelvic laparoscopic procedures where removal of tissue specimens through a colpotomy incision is indicated.

2. Description of the Prior Art

Conventional hysterectomy surgical procedures typically involve one of four approaches—vaginal hysterectomy, total abdominal hysterectomy (TAH), total laparoscopic hysterectomy (TLH), and laparoscopically assisted vaginal hysterectomy (LAVH). Vaginal, TLH and LAVH have become more popular among surgeons because these approaches are less invasive than TAH, with TLH being the least invasive approach. TLH is less invasive than LAVH because it avoids the trauma normally caused by the expansion induced to the vaginal area to permit access of the surgeons hands to the cervical area. Unless medical indications require TAH (such as in the case of tumor removal and the associated need to avoid cell spillage), vaginal, TLH and LAVH are usually viewed as more preferable because each is less invasive when compared to major abdominal surgery. Thus, TLH and LAVH approaches usually result in shorter hospitalization and recovery times.

Difficulty, however, is encountered when employing vaginal, TLH and LAVH techniques due to inherent limitations on visibility, anatomical identification, and the ability to manipulate organs (especially the uterus). In the case of TLH, these limitations are particularly pronounced because of higher degree of difficulty in securing the uterine arteries and cardinal ligaments associated with this approach. A higher degree of surgical difficulty has been found empirically to give rise to an increased risk of inadvertent damage to or dissection into the bladder, ureters, uterine vessels and uterosacral and cardinal ligaments during the surgical procedure. Although the risk of inadvertent damage, for example, to the ureters can be minimized by the insertion of ureteral stints and/or peritoneal dissection to delineate ureter location, such techniques increase the complexity and the cost of the hysterectomy.

Other limitations associated with vaginal, TLH and LAVH surgical approaches, when compared to TAH, include limited exploratory ability and surgical control. Vaginal, TLH and LAVH approaches can also result in the unnecessary shortening of the vagina due to the limitations discussed above.

These difficulties and limitations have slowed the move by surgeons to use of the least invasive surgical approach (i.e., TLH), leading most gynecologists to perform LAVH.

Accordingly, there is a real and unsatisfied need in the surgical arts for a simplified total laparoscopic hysterectomy procedure to accurately secure uterine vessels and cardinal/uterosacral ligaments and to provide for a simplified colpotomy incision without ureteral dissection.

SUMMARY OF THE INVENTION

The present invention overcomes the problems outlined above, and provides a surgical method and assembly allowing accuracy, reproducibility and safety in performing the more challenging portion of a total laparoscopic hysterectomy. In particular, the present invention overcomes the problems outlined above by providing anatomical landmarks and colpotomy incision backstops within the female pelvic cavity to assist physicians and surgeons with visibility and to facilitate incisions that avoid damage to other structures, such as bladders and ureters, and that optimize vaginal length following a hysterectomy. Benefits that accrue in the practice of the instant invention include the preservation of the vaginal length by minimizing unnecessary excision of vaginal tissue and non-division of uterosacral ligaments (with innervation intact and support of the vagina intact). The benefits associated with the instant invention may also accrue in connection when the instant invention is practiced in connection with a TAH.

A colpotomy assembly is provided for use with a simplified total laparoscopic hysterectomy procedure in the form of a colpotomy assembly including an elongated shaft member having a shaft handle mounted in pivotal relationship to a shaft proximal end and a vaginal extender mounted to a distal end of the shaft, the vaginal extender operatively coupled to the shaft handle for articulation of the vaginal extender relative to the frame. The vaginal extender includes structure for engaging a patient's vaginal fornix to provide an anatomical landmark and incision backstop for making colpotomy incisions from a patient's abdominal cavity. The vaginal extender is configured so that when employed by a surgeon during a hysterectomy procedure, the-fornix-engaging structure bears against at least a portion of a patient's vaginal fornix apex to permit a vaginal incision during a hysterectomy that optimizes vaginal length.

In the preferred embodiment, the vaginal extender is in the form of an annular main body having a proximal end integral with a cervix-engaging base and extending distally therefrom and presenting a substantially continuous circular, beveled fornix-engaging rim. The rim is configured to provide the anatomical landmark and incision backstop when inserted for use in a hysterectomy procedure. In alternative embodiments, the vaginal extender is provided with viewing windows disposed on and extending through the outer peripheral cylindrical surface to assist with the mounting of the extender on a patient's cervix so that proper contact is made with the patient's vaginal fornix apex and cervix.

BRIEF DESCRIPTION OF THE DRAWINGS

FIG. 1 a side elevational view showing a colpotomy assembly with a vaginal extender mounted on a uterine manipulator and tip.

FIG. 2 is a bottom plan view of the colpotomy assembly.

FIG. 3 is top plan view of the colpotomy assembly.

FIG. 12 is an enlarged, perspective elevational view of the vaginal extender.

FIG. 13 is an enlarged, perspective elevational view of an alternative embodiment of the vaginal extender.

FIG. 14 is an enlarged, side elevational view of the vaginal extender.

FIG. 15 is an enlarged, side cross-sectional view of the vaginal extender taken along line 15—15 in FIG. 14.

FIG. 16 is a top plan view of the vaginal extender.

FIG. 17 is a side elevational view showing the half-cup vaginal extender alternative embodiment.

FIG. 18 is an enlarged, top plan view of the half-cup vaginal extender alternative embodiment.

FIG. 19 is a perspective view of the finger vaginal extender alternative embodiment.

FIG. 30 is a front elevational view showing an opening in the distal end of the alternative occluder.

FIG. 31 is a side sectional view of the alternative occluder showing the balloon cuff in a deflated configuration.

FIG. 32 is a side elevational view of the alternative occluder showing distal and proximal ends.

FIG. 33 is a side elevational view showing a colpotomy assembly with an alternative occluder mounted on the shaft with a vaginal extender sandwiching the distal end of the occluder between the base and the extender.

FIG. 34 is an enlarged partial sectional view showing the distal end of the alternative occluder sandwiched between the extender and tip base.

DETAILED DESCRIPTION OF THE PREFERRED EMBODIMENT

Description of the Colpotomy Assembly

Figure 5:
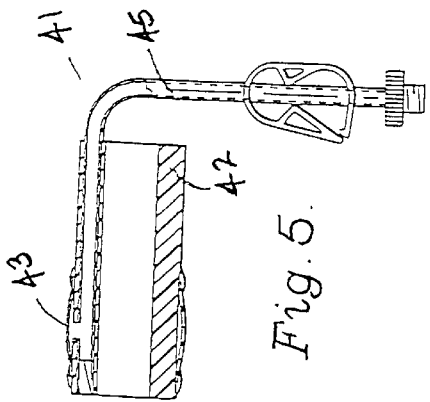
FIG. 5 is a cross-sectional, elevational view of the vaginal occluder showing the fluid conduit and balloon cuff uninflated.
Figure 4:
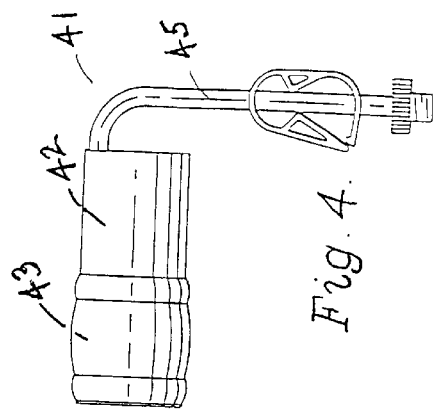
FIG. 4 is a side plan view of the vaginal occluder.
Figure 6:
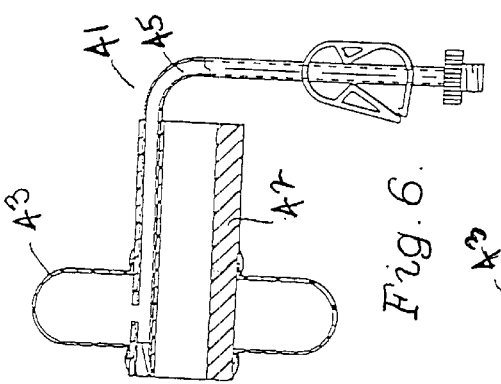
FIG. 6 is a side, cross-sectional elevational view of the vaginal occluder showing the balloon inflated.
Figure 7:
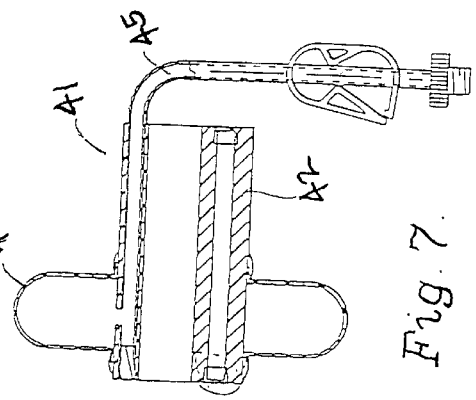
FIG. 7 is a side, cross-sectional elevational view of an alternative body of the vaginal occluder showing a surgical instrument access port extending through the occluder main body.
Figure 8:
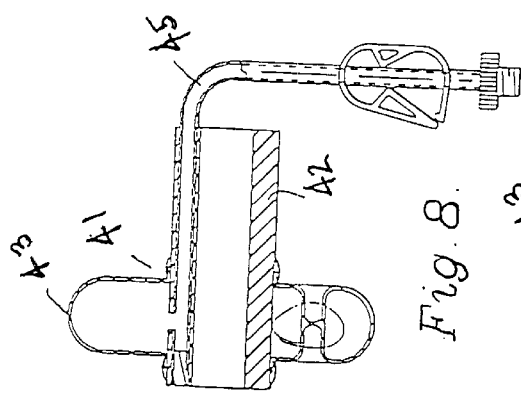
FIG. 8 is a side, cross-sectional elevational view of an alternative body of the vaginal occluder showing a surgical instrument access port disposed in the balloon cuff portion.
Figure 10:
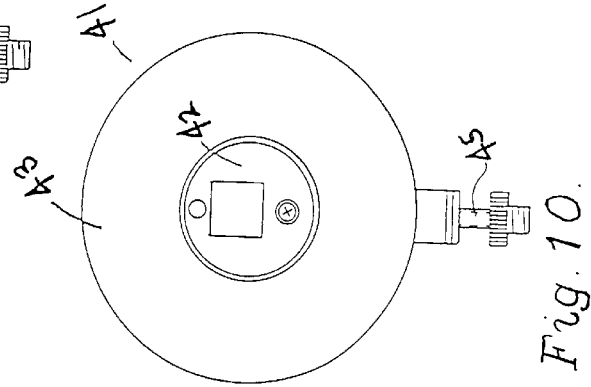
FIG. 10 is a front elevational view of the alternative embodiment of the occluder with the cuff inflated and showing the surgical instrument access port disposed in the occluder main body.
Figure 9:
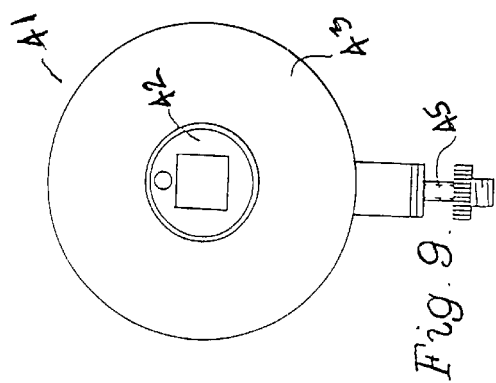
FIG. 9 is a front elevational view of the vaginal occluder showing the cuff inflated.
Figure 11:
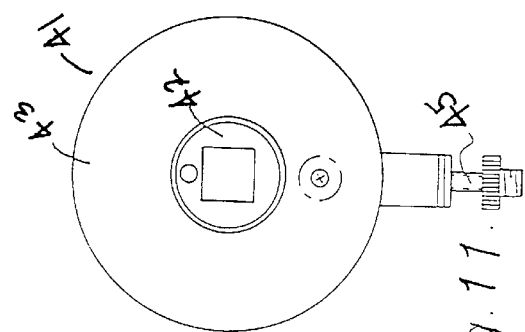
FIG. 11 is a front elevational view of the alternative embodiment of the occluder with the cuff inflated and showing the surgical instrument access port disposed in the inflated balloon cuff.

Referring now to the drawings, the colpotomy assembly 10 used in the practice of the instant invention includes a uterine manipulator 16 and a vaginal extender 20.

Uterine manipulator 16 may be any uterine manipulating device known in the art, and in the preferred embodiment is a Rumi™ uterine manipulator such as that shown in U.S. Pat. No. 5,409,496, the teachings of which are incorporated by reference (Cooper Surgical, Shelton, Conn., 06484). As shown in FIGS. 1–3, uterine manipulator 16 includes an elongated frame 26, a handle 28, a tip mount 30 configured to be removable, a uterine manipulating tip 32, base 33 presenting a distal face 33a, and a locking mechanism 34. The frame 26 defines a proximal end 38 and a distal end 40. A vaginal occluder 41 is slidably received by frame 26 and includes a main body 42 including an outwardly presented balloon cuff 43.

A fluid conduit 44 is affixed to balloon cuff 43 through which fluid flows to balloon cuff 43 for inflation. In the preferred embodiment, occluder 41 is constructed of a medical grade silicone suitable for injection molding. Occluder 41 may also be provided with an access port 45 and is configured to permit the insertion of surgical tools therethrough.

Handle 28 is affixed in pivotal relationship to the frame proximate end 38. The tip mount 30 is affixed in pivotal relationship to the frame distal end 40. It will be appreciated that distal end 40 is configured to be inserted into the vaginal cavity 48 of a patient during use of the manipulator 16 in the course of examination or surgery, while the proximate end 38 remains exterior to the patient's body.

The tip 32 includes a natural or synthetic rubber body 50 (as used herein, the term "synthetic rubber" is intended to include within its meaning silicone compounds) with dye conduit 62 communicating with a tip bore 64 extending through finger 66. The tip also includes a balloon conduit 68 to communicate with an expandable balloon 70 surrounding the finger 66.

The uterine manipulator 16, in the preferred embodiment, also includes a locking mechanism 34 which serves to connect and fix handle 28 relative to frame 26. Connecting structure 78 operatively couples tip mount 30 to handle 14.

The vaginal extender 20 includes an annular main body 90 and includes a base 92 at its proximal end 94 and a fornix-engaging, circular rim 96 at its distal end 98. Circular rim 96 is beveled, as shown in FIGS. 14–19, to permit an anatomical landmark and incision backstop during use. Vaginal extender 20 is formed of any medical grade plastic material commonly known to those skilled in the art and obtainable from conventional suppliers. The extender 20 may alternatively be formed of any material of construction suitable for the use described below, including stainless steel or a rigid gauze composite. The annular body 90 presents an outer peripheral, generally cylindrical surface 102 which extends between the-fornix-engaging rim 96 and base 92. A laterally-extending slot 103 is positioned on the cylindrical surface 102 to permit use of surgical instruments as later explained.

Viewing windows 104 may be disposed in and extend through the outer cylindrical surface 102, as shown in FIG. 18.

Base 92 includes a proximate end 108 presenting socket 112 for captively receiving the uterine manipulator tip base 33. Base 92 further includes an aperture 116 extending between socket 112 and the annular main body 90 for receiving manipulator tip 32 when vaginal extender 20 is mounted on uterine manipulator 16, as shown in FIGS. 14–16. Aperture 116, in an alternative embodiment, has a diameter significantly larger than that associated with tip 32 (but smaller than the diameter associated with socket 112) to provide a view of the cervix 136 for situations where the extender 20 is placed into position before the uterine manipulator 16 is inserted into the uterus 130.

When vaginal extender 20 is mounted on the uterine manipulator 16, manipulator tip 32 extends axially through annular body 90, as shown in FIG. 1.

The dimensions of the vaginal extender 20, in the preferred embodiment, will now be described. Referring to FIGS. 14–16, the inner diameter 138*a* is between 0.99 inch and 1.18 inches, depending on anatomical indications. Rim 96 has a beveled angle 138*b* of 42 degrees. The outer diameter 138*c* of the annular main body 90 is about 1.246 inches to 1.436 inches, depending upon anatomical indications. The outer diameter 138*d* of base end 108 is about 1.0 inch. The inner diameter 138*e* of socket 112 is about 0.79 inches. The taper angle 138*f* of the interior surface 139 of annular main body 90 is about 99 degrees. The width 138*g* of lateral slot 103 is about 0.156 inches. The internal diameter 138*h* of aperture 116 is about 0.63 inches. The length 138*i* of annular main body 90 is about 0.815 inches. Referring to FIG. 19, the reference dimensions 138*j* and 138*k* associated with windows 104 are 0.187 inches and 0.50 inches, respectively. The depth 138*l* of socket 112 is 0.450 inches. The taper angle 138*m* of the base 92 is between 81 degrees and 90 degrees depending on anatomical indications.

Although specific dimensions are disclosed above for one of the preferred embodiments of the vaginal extenders 20, other factors may indicate the need for different shapes and sizes.

Insertion of the colpotomy assembly 10 into the vaginal cavity 48 with tip 32 inserted into the uterus 130 is largely similar to the procedures well known in the prior art for the insertion of uterine manipulators. A tenaculum can be used to aide the insertion of tip 32 into the uterus 130 by placing the tenaculum into slot 103 during use. FIGS. 21, 22, 25 and 29 illustrate the colpotomy assembly 10 after it has been inserted for use in the practice of the instant invention. When inserted, cervix 136 is received into the annular main body 90 of the vaginal extender 20 and rim 96 is placed into engaging relationship with the apex 140 of fornix 142. Windows 104 are provided in the vaginal extender 22 to permit the viewing of the cervix 136 during the engagement of the vaginal extender 20 with cervix 136 and vaginal fornix apex 140. Uterine manipulator tip 32 is fully inserted in the uterus 130 and balloon 70 is inflated to come into engaging relationship with the uterus interior surface 146.

A vaginal extender 20 may have any shape or dimension suitable for use during hysterectomies involving colpotomy incisions provided that its shape and dimension is sufficient to delineate the anatomical landmarks and to provide incision backstops so that the surgical procedure will be simpler and safer and result in optimal vaginal length following the hysterectomy. Examples of alternative embodiments of extender 20 are shown in FIGS. 13, 16–18. Shown in FIG. 13 is a vaginal extender 20 with a base 92 having an outer peripheral surface which is cylindrical rather than tapered. Shown in FIGS. 17 and 18 is a "half-cup" vaginal extender 143. Shown in FIG. 19 is a finger vaginal extender 144. Extenders 143 and 144 are used in ways substantially identical to those described for vaginal extender 20. However, the particular shapes of extenders 143 and 144 may be indicated or otherwise advantageous based upon the anatomy of a particular patient.

Once the colpotomy assembly 10 is inserted into the vaginal cavity 48, the occluder 41 may be inflated to seal the distal vaginal cavity 150 from the proximal vaginal cavity 152. In the preferred embodiment, occluder 41 is inflated with sterile, water-based fluid because the preferred, silicone-based material of construction of the occluder cuff 43 is gas permeable. However, in applications where gas leakage from occluder 41 can be tolerated, air can be used to inflate cuff 43.

Figure 22:
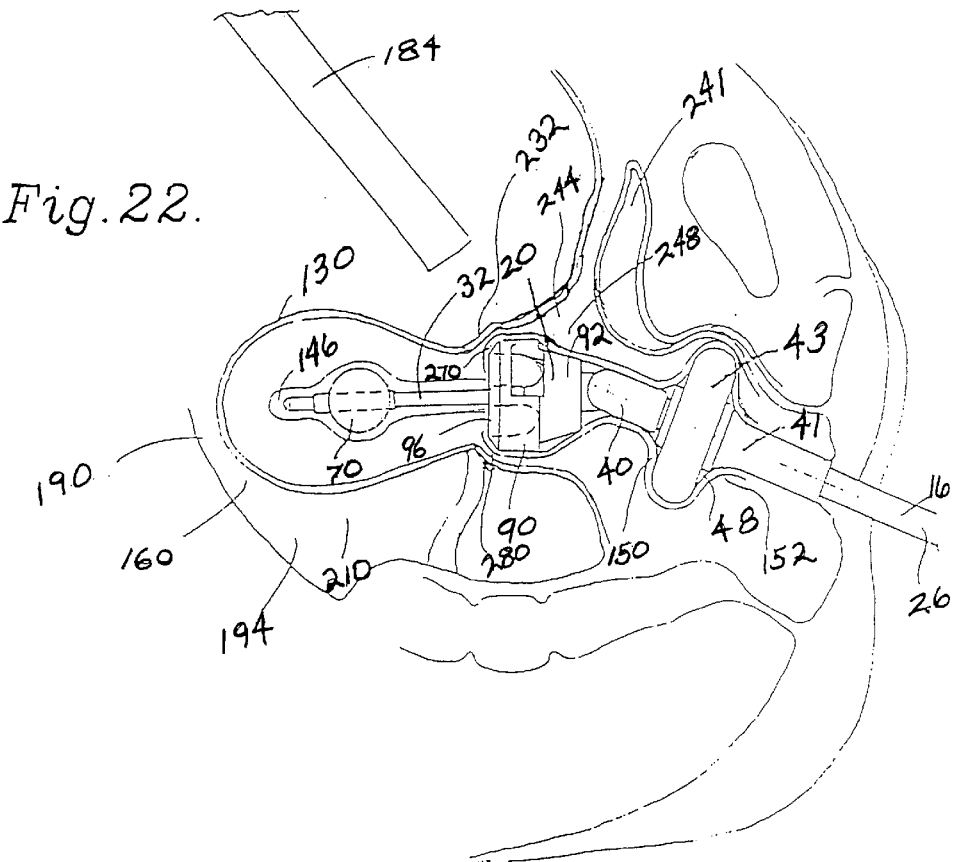
FIG. 22 is a cross-sectional, side view of the pelvic cavity showing the colpotomy assembly holding the uterus in an retroverted position.
Figure 25:
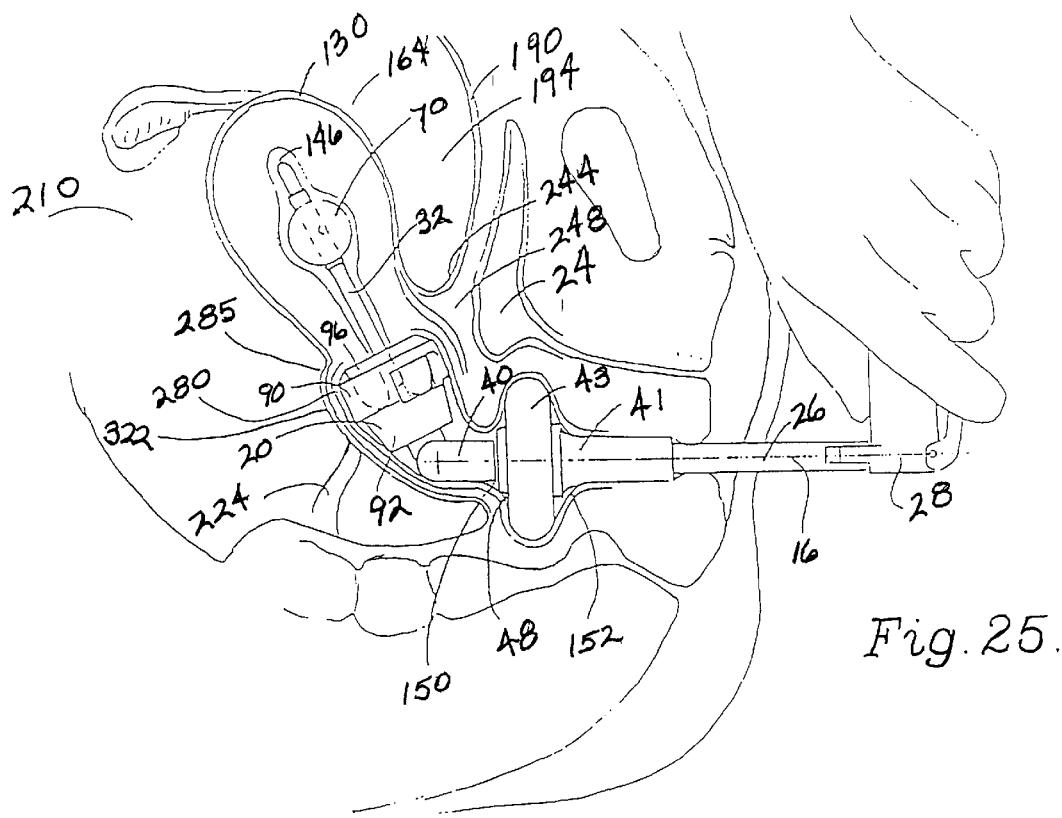
FIG. 25 is a cross-sectional, side view of the pelvic cavity showing the colpotomy assembly holding the uterus in an anteverted position.
Figure 23:
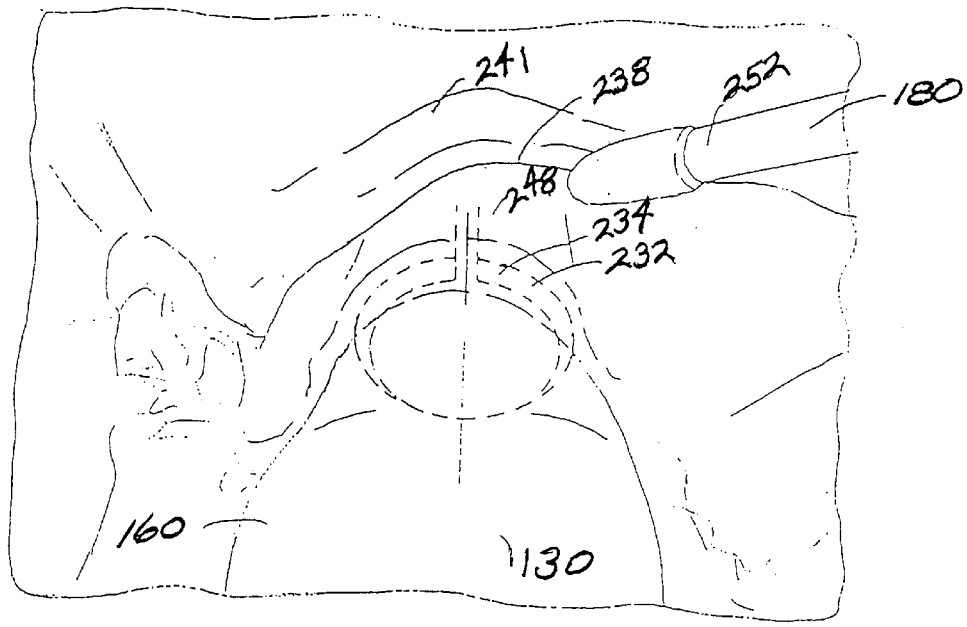
FIG. 23 is a frontal view of the retroverted uterus in the abdominal cavity.
Figure 24:
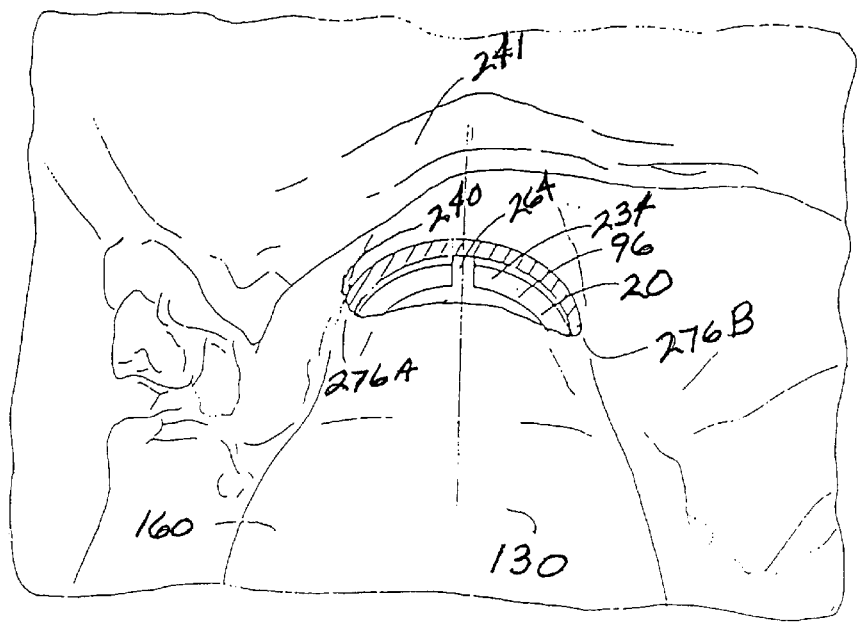
FIG. 24 is a frontal view of the retroverted uterus in the abdominal cavity showing the anterior rim portion.
Figure 26:
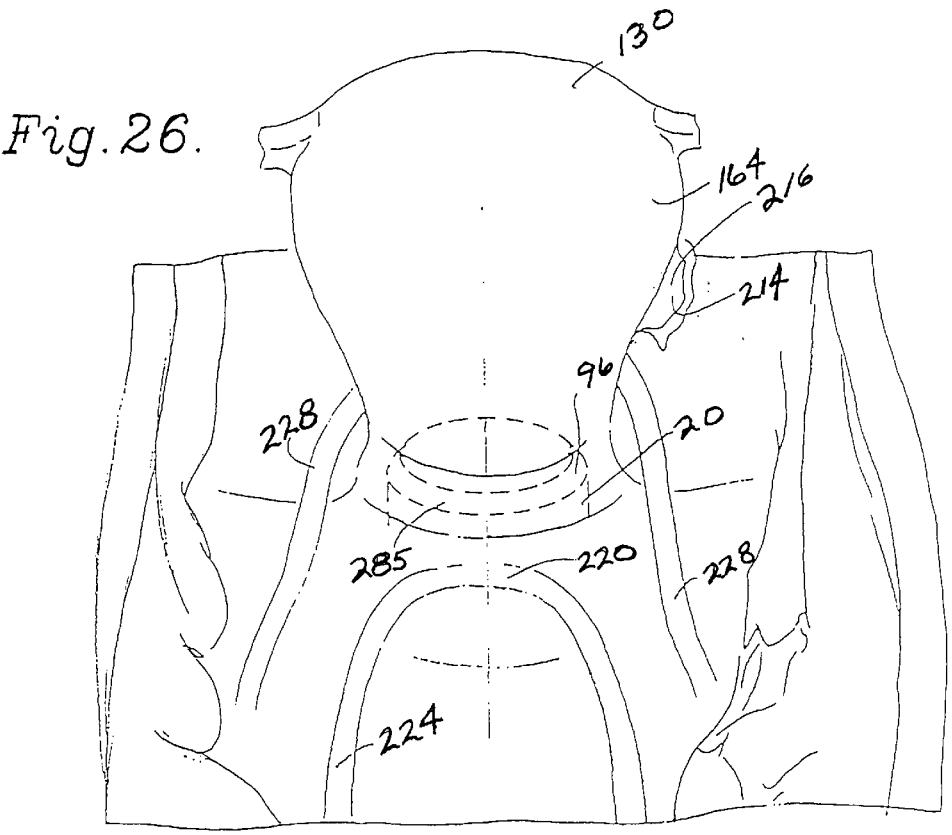
FIG. 26 is a frontal view of the anteverted uterus in the abdominal cavity.
Figure 27:
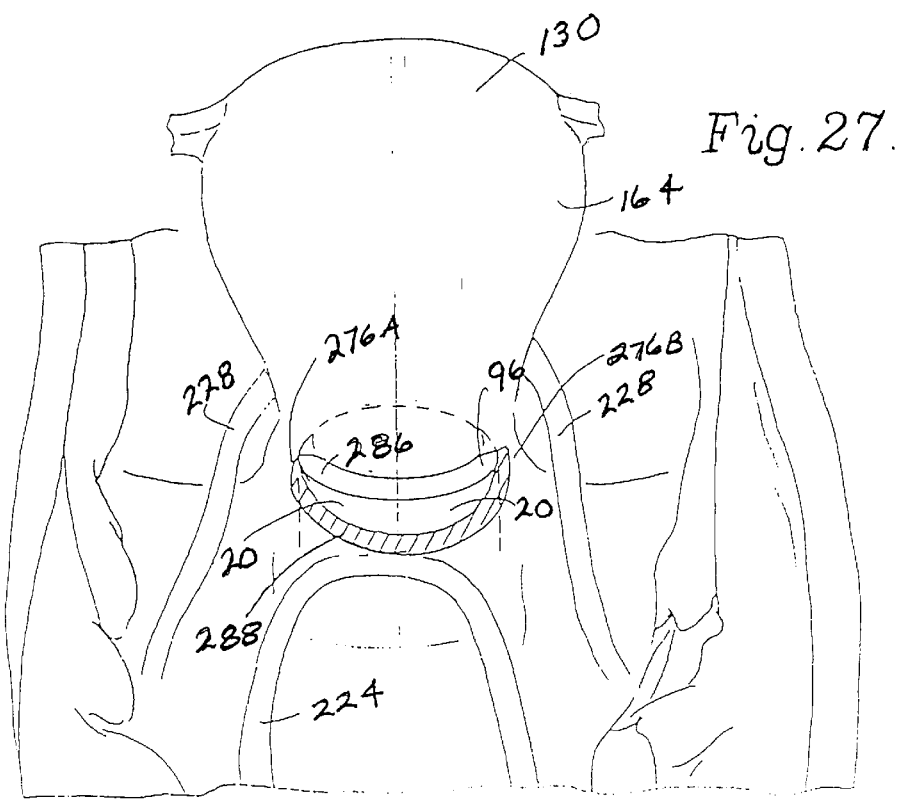
FIG. 27 is a frontal view of the anteverted uterus in the abdominal cavity showing the posterior rim portion.
Figure 28:
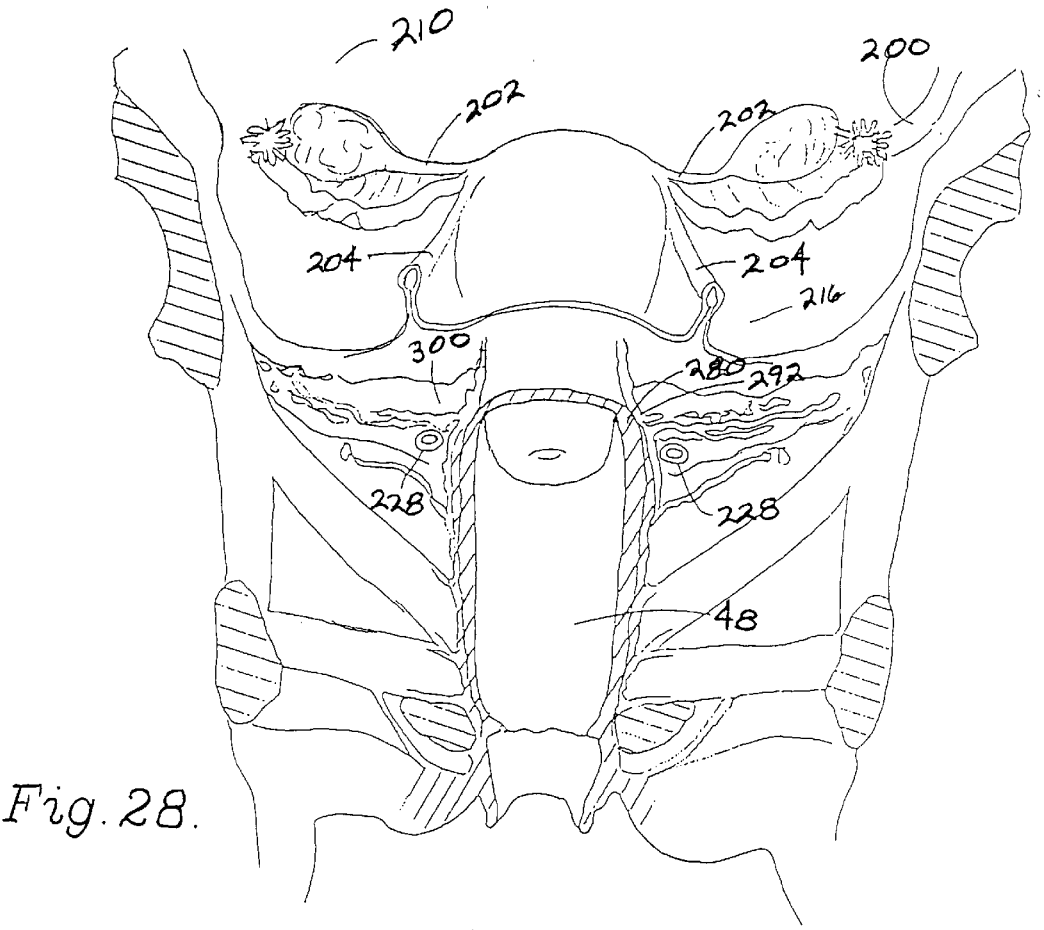
FIG. 28 is a cross-sectional view of a female pelvic cavity showing the position of various ligaments, blood vessels and ureters.

When a surgeon or physician desires to manipulate the uterus into a retroverted position, he simply articulates handle 28 in relation to frame 26 in the appropriate rotational direction. Articulated rotation of handle 28 causes the tip base 33, the uterine manipulator tip 32, and the vaginal extender 20 mounted thereto, to articulate and pivot in relationship to frame 26, placing uterus 130 in a retroverted position 160, as shown in FIGS. 22–24. To manipulate the uterus into an anteverted position 164, the surgeon or physician articulates handle 28 in the opposite rotational direction, which articulated rotation causes a corresponding articulated rotation of tip base 33, uterine manipulator tip 32, vaginal extender 20, and the engaged uterus 130, which moves uterus 130 into the anteverted position 164, as shown in FIGS. 25–27. The locking mechanism 34, if provided, serves to prevent undesired return of the uterus 130.

Description of the Simplified Total Laparoscopic Hysterectomy Method Employing Colpotomy Incisions The simplified total laparoscopic hysterectomy (TLH) method of the instant invention will now be described. A patient is prepared for TLH surgery according to procedures which are well known in the surgical arts and will not be repeated here. Once prepared, the abdominal cavity is inflated to facilitate the accessibility to and visibility of the female pelvic organs. Surgical instruments 180, including a laparoscope 184, are inserted through the abdomen wall 190 into the abdominal cavity 194.

A uterine manipulator, such as the colpotomy assembly 10 described above, is inserted into the vaginal cavity 48, as shown in FIGS. 21, 22, 25 and 29.

Upper Pedicles

The tubo-ovarian pedicle and suspensory ovary ligaments 200, proper ovarian ligaments 202, and round ligaments 204, are divided either medial or lateral to the ovary depending on whether oophorectomy is indicated, using a variety of conventional methods for incisions, ligation, and desiccation, for example, bipolar, stapler cutter, suture, endo-loop, as appropriate. The round ligament 204 is most conveniently bipolar desiccated and divided and allows the opening of the parametrial space 210. At this point, the posterior leaf 214 of the broad ligament 216 is divided by scissors or unipolar cautery down towards the immediate lateral aspect 220 of the uterosacral ligament 224. This division will allow lateral mobilization of the ureters 228.

Uterovesical Peritoneum

Figure 21:
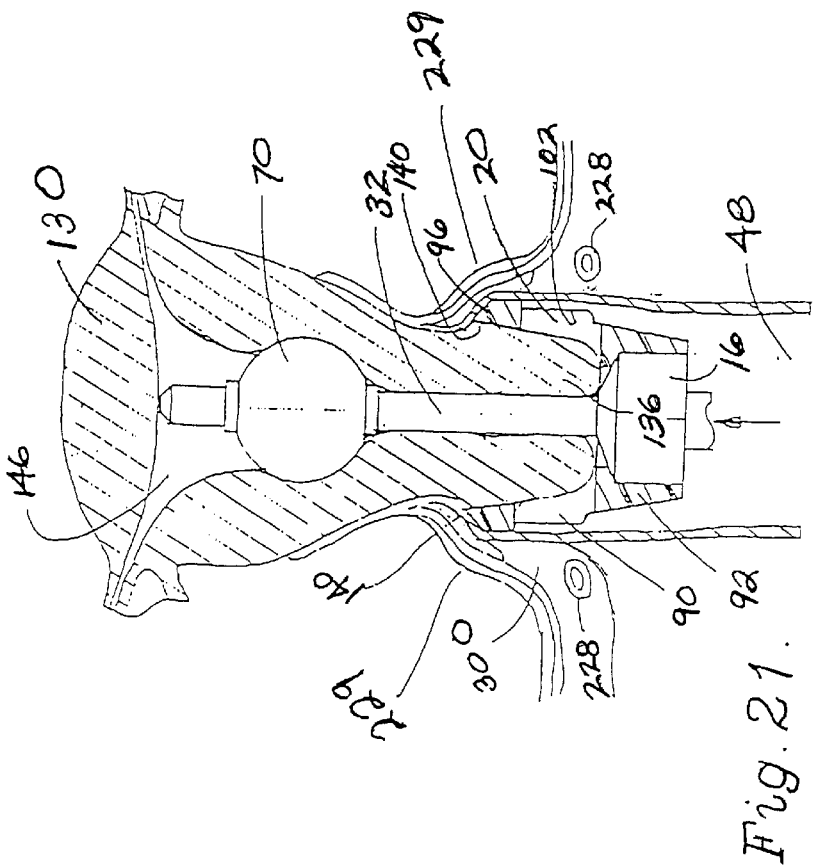
FIG. 21 is an anterior, cross-sectional view of a uterus showing the vaginal extender inserted and extended into the vaginal fornix apex following the cephalad push.
Figure 20:
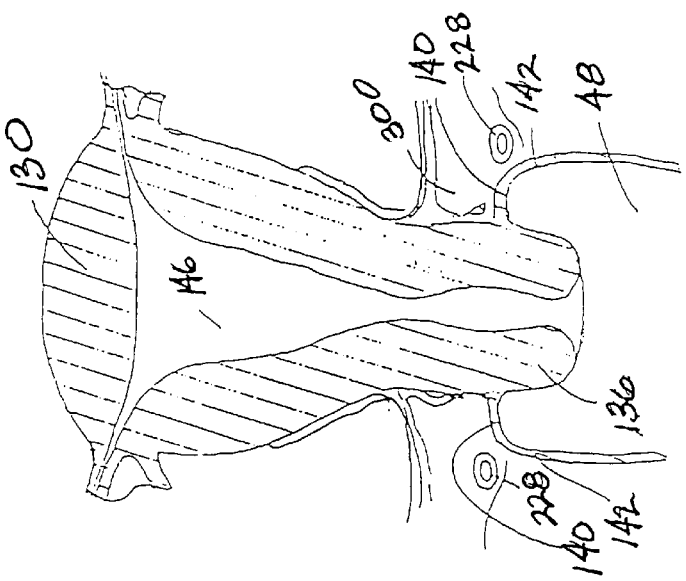
FIG. 20 is an anterior, cross-sectional view of a uterus.

The colpotomy assembly 10 is adjusted to position the uterus 130 in a retroverted position 160 making the vaginal extender 20 easily visible. A cephalad (toward the head) push on the colpotomy assembly 10 causes further tenting 229 of the vaginal fornix 142, as shown in FIG. 21. A first anatomical landmark and incision backstop 232 is provided by anterior rim portion 234 of the rim 96 of vaginal extender 20 indicates the area of loose uterovesical peritoneum 138 where the incision 240, to reflect the bladder 241, will begin. The incision is performed again using scissors (or other dissecting tools), with unipolar or bipolar hemostasis as infrequently needed. The bladder peritoneum 244 is then elevated with a grasper 180 and the areolar tissue 248 may be pushed down towards the vagina against the anterior of main body 90 of the vaginal extender 20, using a Kittner 252. Alternatively, a sharp dissection will be made with the use of scissors cutting and dissecting the correct plane in the pubocervical fascia 256, which is avascular. It will now be easy to push the bladder 241 down some 2 cm from the vaginal fornix apex 140. The bladder 241 may be temporarily filled at this stage with methylene blue to indicate its position and intactness. The bladder pillars (not shown) may be laterally bipolar desiccated or unipolar divided, and further lateral reflection of the bladder 241 in a caudal direction is performed, using the Kittner 252 or other blunt probe. The lateral reflection of the bladder 241 in the caudal direction has the effect of pushing the ureters 228 laterally and inferiorly, aided by the previously divided posterior leaf 214 of the broad ligament 216.

Anterior Colpotomy

After positioning the uterus 130 in the retroverted position 160 and making a cephalad push of the colpotomy assembly 10 against the uterine cervix 136, an anterior colpotomy incision 264 is made over the anatomical landmark and incision backstop 232 provided by anterior portion 234 of rim 96. The anterior incision 264 is made using a unipolar electrode or other form of energy. The fornix-engaging rim 96 allows an accurate incision into the anterior vaginal fornix 270. The anterior colpotomy incision 264 extends laterally short of the lateral vaginal angle 276 on both sides 276a and 276b, as shown in FIG. 24.

The presence of the anatomical landmark and incision backstop 232 provided by the colpotomy assembly 10 ensures that dissection of the vagina 280 and parametrium 284 is accurate and does not proceed more caudal than is necessary. This is often the case where the apparatus and method of the instant invention is not employed because of the distorted visualization at laparoscopy and the inability to determine the location of the vaginal fornix apex 140.

The vaginal occluder 41 prevents the escape of gas used to inflate the abdominal cavity 194 during and following the first of any colpotomy incision, which, in the preferred practice, is the anterior colpotomy incision 264.

Posterior Colpotomy

The uterus 130 is now repositioned into the anteverted position 164 so that the fornix-engaging rim 96 is easily visible and palpable. The fornix apex 140 is now above the insertion of the uterosacral ligament 224. Therefore, it is not necessary to divide the uterosacral ligament 224 in order to perform a posterior colpotomy, thereby preserving existing uterine support and innervation and minimizing the bleeding that follows uterosacral transection. Furthermore, the ureters 228 are not endangered by division of the uterosacral ligament 224. A second anatomical landmark and incision backstop 285 is provided by a posterior portion 286 of rim 96, as shown in FIG. 26. A posterior colpotomy incision 288 is performed by reference to and by making an incision over the second anatomical landmark and incision backstop 285. The posterior colpotomy incision 288 is performed similar to the anterior colpotomy incision 264 and is made laterally up to but short of the lateral vaginal angles 276 on both sides 276a and 276b.

Although in the preferred practice, the anterior colpotomy incision 264 is made before the posterior colpotomy incision 288, the order may be reversed.

Uterine Vessel/Cardinal Ligament Pedicle

After anterior incision 264 and posterior incision 288 have been made, the uterine vessels 292, with appropriate uterine manipulation, can be made visible and desiccated just at the level of the lateral fornix 296 as indicated by the fornix-engaging rim 96 and the anterior and posterior colpotomy incisions 264 and 288, respectively. With the elevation of the uterus 130 in the anteverted position 162, the ureters 228 are now more than 2 cm inferior and lateral to the uterine vessel oblique cardinal pedicle 300 that will now be secured with bipolar desiccation or suture ligation.

Figure 29:
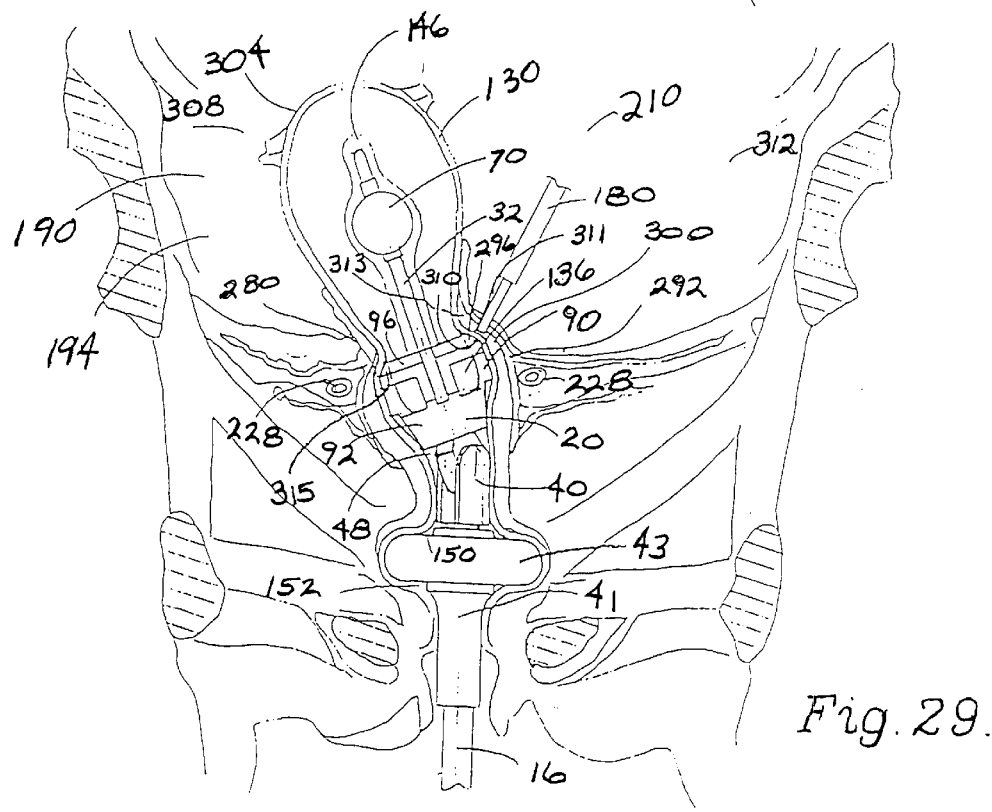
FIG. 29 is a top plan, cross-sectional view of the abdominal cavity showing the fundus moved against the inner pelvic wall.

To perform the desiccation of the uterine vessels 292 and colpotomy of the cardinal pedicle 300 located at the lateral vaginal angle 276a, as shown in FIG. 29, the uterus fundus 304 is positioned as needed towards the opposite pelvic side wall 308, which delineates the third anatomical landmark and incision backstop 310 created by a first lateral rim portion 311. The uterine vessels 292 are now visible and are bipolar desiccated at the level of the vaginal fornix apex 140 as indicated by the third anatomical landmark and incision backstop 310 and by the anterior and posterior colpotomy incisions 264 and 288, respectively. Following this, the uterine vessels 292 are divided. The cardinal ligament zone 313 presented by the divided uterine vessels 292 can now be easily and safely divided, as shown in FIG. 29. The lateral vaginal angle 276A is now incised, joining the corresponding ends of the anterior and posterior colpotomy incisions 264 and 288, respectively.

The same procedure as that explained above for the incision at lateral vaginal angle 276a is performed on the opposite lateral vaginal angle 276b after first manipulating fundus 304 as needed towards the pelvic side wall 312 opposite lateral vaginal angle 276b. It is to be understood that the order of making incisions at lateral vaginal angles 276a and 276b, as described above, may be reversed.

Once the fundus 304 is so positioned, a fourth anatomical landmark and incision backstop 314 is presented by second lateral rim 315. After the vaginal lateral angle 276B is incised, the uterus 130 is totally free in the abdominal cavity 194 and held only by the colpotomy assembly 10.

Removal of Uterus

The vaginal occluder 41 is now deflated and the colpotomy assembly 10 removed through the vagina 280. A tenaculum may be used on the cervix 136 to aid in pulling out an enlarged uterus 130. The colpotomy assembly 10, with the vaginal extender 20, tip 32, and tip base 33 removed, may be reintroduced into the vagina 280 to provide vaginal manipulation and pneumo-occlusion while vaginal closure takes place abdominally. Alternatively, vaginal closure may take place vaginally at this stage.

Closure of the Vagina

The vaginal cuff 318 can be closed by any method known in the surgical arts, including the use of three mattress sutures laparoscopically, using intracorporeal tying (not shown). The right vaginal angle 276a is secured in the mattress suture that incorporates the cardinal pedicle 300 and is tied anteriorly. The left vaginal angle 276b is similarly secured. The center of the vaginal cuff 318 is then secured with a single mattress suture and tied anteriorly. Any bleeding points are bipolar desiccated without fear of releasing the sutures as they are under the surface of the vagina 280.

If there is descent, various methods of colposuspension may be attempted. A potential enterocele may be closed, using the Moschcowitz, Halban's or McCall culdoplasty method or other variations thereof.

With respect to the order of making colpotomy incisions 264, 288, and incisions at lateral vaginal angles 276a, 276b, it is to be understood that any order may be employed for making such incisions. For example, the incisions at lateral vaginal angles 276a, 276b may be performed prior to colpotomy incisions 264 and 288. Further, the incisions may be made in a clock-wise or counter clock-wise pattern beginning from any anatomical landmark as desired.

Laparoscopic Rescue of Vaginal Hysterectomy

While many instances of abdominal hysterectomy are performed preemptively in the belief that the vaginal hysterectomy will not succeed either from lack of decent or other complicating factors, many cases that originate vaginally are similarly converted to an abdominal hysterectomy when progress from below has ceased. The colpotomy assembly 10 and the associated method of the instant invention, however, may likewise be used to rescue a failed vaginal hysterectomy if abdominal rescue is undesirable. Such a rescue can be performed without a need of performing a laparotomy. Depending on whether the vaginal incision has been completed and whether the anterior and posterior peritoneum have been incised, the use of the vaginal extender 20 may be included or excluded. However, the use of the colpotomy assembly 10 is needed, with the vaginal extender 20, tip 32, and base 33 removed, because vaginal occluder 41 is needed for completion of the procedure.

Other Indications for Using the Colpotomy Assembly

Tissue removal may be facilitated by the use of the colpotomy assembly 10. This invention is particularly useful for removing large abdominal masses during laparoscopic surgical procedures. Traditionally, large mass removal during laparoscopic surgery has presented a problem to the surgeon because the only means to laparoscopically remove the mass would be to pull the mass through an existing trocar hole, which would typically be no greater than 12 mm in diameter. Because large diameter masses will not physically fit through a trocar hole, various mechanical devices to morcellate the tissue have been devised and are well known to those skilled in the art. While the general technique of tissue morcellation as a means to extract abdominal masses has been shown to be effective, the mechanical devices required can be costly and also represent additional risk to the patient during surgery if not used correctly.

Another traditional means of removing the large abdominal mass during laparoscopic surgery has been to surgically increase the size of the trocar hole in the patient's abdomen, making it large enough to allow the abdominal mass to exit the body. This method is sometimes referred to as a "mini-laparotomy". While generally effective, the mini-laparotomy technique subjects the patient to additional trauma from the increased abdominal incision, thus requiring a longer recovery period as well as leaving larger visible tissue scaring which is undesirable to many patients for cosmetic reasons.

As an alternative to the traditional methods of removing masses from the abdomen, including large tissue masses, the colpotomy assembly 10 can be used to facilitate removing abdominal tissue by extracting the tissue through a colpotomy incision into the vagina where it can be easily removed from the patient's body. The rim 96 of the colpotomy assembly 10 delineates the position for incising the fornix 142 for hysterectomy.

Lower vaginal cavity tissue may also be removed using the invention. When a colpotomy is required in the lower region of the vaginal cavity 322, an incision may be performed by the delineation of vaginal tissue by the lower margin of the annular main body 90 of vaginal extender 20. The vaginal extender 20 is configured such that an incision at the lower margin of the annular main body 90 can be made at a location far enough away from rectum to avoid injury, particularly in cases where there might be mild adherence of the rectum to the posterior fornix 326 as in endometriosis. The vaginal occluder, 41, may remain inflated during tissue removal through the colpotomy incision in order to maintain the pneumo-peritoneum and allow the laparoscopic surgery to proceed without interruption due to loss of gas pressure in the abdomen. When in use during surgery as part of the colpotomy assembly 10, the physical position of the vaginal occluder 41 in the vagina allows sufficient space between the vaginal occluder 41 and the distal end of the vagina for tissue to be extracted from the abdomen, through the colpotomy incision, and into the vagina for temporary storage while the surgery proceeds laparoscopically. Once the laparoscopic portion of the surgery is complete, the vaginal occluder 41 may be deflated allowing access to the abdominal tissue for removal from the vagina.

Rectovaginal Space Dissection with the Use of the Colpotomy Assembly

Cases of Rectovaginal endometriosis that involve the vaginal wall may be dissected satisfactorily and excision of the lesion including the posterior vaginal wall may be satisfactorily performed without difficulties associated with loss of pneumoperitoneum. The rigid posterior vaginal wall with the colpotomy assembly against it will also help dissection of the adherent rectum from the vagina. The excised endometriotic mass may also be removed through the vagina with or without a bag.

Bowel Resection Via Colpotomy

The step of bowel resection anastomosis which involves exteriorization of the proximal sigmoid loop in order to place the EEA tip may now be done through the colpotomy incision and then returned to the abdominal cavity 194 for completion of the anastomosis without the need to extend an abdominal wound.

Alternatively, the total anastomosis resection may be performed through the colpotomy incision as described by Redwine.

It will be appreciated that there are a variety of techniques and devises for making incisions and for stopping bleeding which may be employed in connection with the practice of the instant invention. For example, incisions, desiccation, ligation and hemostasis may be accomplished by techniques and devices such as mono-polar and bi-polar cutting devices, stapler cutting devices, sutures, simple staplers, scalpels and combinations thereof. While the preferred techniques and devices are disclosed above for making incisions and stopping bleeding (desiccation, ligation, and hemostasis), any suitable means for making incisions or stopping bleeding may be employed when practicing the invention.

Alternative Occluder Embodiment

Alternative vaginal occluder 441 includes a main body 442 shaped like a fully extended condom and including an outwardly presented balloon cuff 443, fluid conduit 444, and main body distal and proximal end 450, 452. Occluder 441 may be constructed from any suitably elastic material such as medical grade silicone elastomer. The distal end 450 includes an opening 456 having a diameter larger than the uterine manipulator tip 32 and smaller than that of the uterine manipulator tip base 33. In particular, opening 456 is sized relative to the diameter of tip 32 and tip base 33 to permit occluder 441 to be slidably received on frame 26, as shown in FIG. 30, by pulling the proximal end 452 over the tip 32 and base 33, so that main body 442 receives frame 26 within the annular portion of main body 442. Further, occluder 441 is positioned on frame 26 so that the distal end 450 abuts against and is generally centered on distal face 33a of base 33. The annular body 90 of vaginal extender 20 may now be mounted on base 33 with distal end 450 sandwiched therebetween. Once occluder 441 is installed on frame 26 in the above described fashion and distal end 450 is sandwich between the base 33 and annular body 90 of the vaginal extender 20, a seal is formed therein to prevent the flow of fluid (including gases) between extender 20 and tip base 33 during surgical procedures as described above. The sandwich-like engagement of the distal end 450 between base 33 and annular body 90 also anchors the distal end 450 to base 33 when proximal end 452 is caused to be stretched in a direction opposite distal end 450.

Balloon cuff 443 is attached to an integral width of distal end 450. In the preferred embodiment, balloon cuff 443 may be formed by folding an occluder end back onto and brought into sealing engagement (by means of flexible glue such as RTV or liquid silicone rubber) with the outer surface of occluder 443. A fluid conduit 444 is affixed to balloon cuff 443 and communicates fluid to balloon cuff 443 when inflation is desired.

In use, the colpotomy assembly 10, with the occluder 441 mounted thereon, is inserted into the vaginal cavity 48. Occluder 441 may be inflated to seal the distal cavity 150 from the proximal cavity 152. It will be appreciated that the "condom like" construction of the vaginal occluder 441, when installed and inflated during surgical use, allows the uterine manipulator 16 to move about freely within the vaginal cavity while still maintaining a pressure seal between distal cavity 150 and proximal cavity 152.

We claim:

1. A colpotomy assembly adapted for insertion into a vaginal cavity for use in female pelvic surgical procedures employing the inflation of an abdominal cavity with a gas to facilitate the accessability to and visibility of female pelvic organs, said assembly comprising:

an elongated shaft member presenting a proximal end and a distal end, said distal end of said shaft configured to be inserted into the vagina;

a shaft handle mounted in pivotal relationship to said proximal end;

a vaginal extender having structure for bearing against a patient's vaginal fornix to provide an anatomical landmark for use in making colpotomy incisions from the abdominal cavity into the vagina; said extender attached at a joint to said shaft distal end; said extender operatively coupled to said shaft handle for articulation of said extender relative to said frame; and sealing means associated with said shaft and operable to form a seal with the vaginal cavity to prevent an inadvertent deflation of the abdominal cavity following an incision that permits the flow of gas from the abdominal cavity to the vaginal cavity.

2. The assembly of claim 1, said sealing means being in the form of an inflatable occluder.

3. The occluder of claim 2, said occluder being in flexible engagement with said shaft to permit relative slidable movement therebetween.

4. The assembly of claim 1, wherein said sealing means comprises a vaginal occluder having an annular cuff releasably mounted in circumscribing relationship around said shaft member, said vaginal occluder being inflatable to inhibit the passage of fluid through the vaginal cavity.

5. The assembly of claim 4, further comprising a tip mount mounted to said distal end of said shaft and a tip carried on said tip mount configured to engage a uterus and wherein the vaginal extender receives said tip mount and said tip.

6. The assembly of claim 5, wherein said vaginal occluder includes a main body having a first end thereof retained between said tip mount and said vaginal extender to inhibit the passage of fluid therebetween.

7. A uterine manipulating assembly for insertion into a vaginal cavity for use in female pelvic surgical procedures, said assembly comprising:

a uterine manipulator having an elongated shaft presenting a proximal end and a remote end, and a tip mount mounted to said remote end, said remote end being adapted for insertion into a vaginal cavity;

a tip carried on said tip mount configured to engage a uterus; and a vaginal occluder having an annular cuff releasably mounted in circumscribing relationship around said shaft, said vaginal occluder being inflatable to inhibit the passage of fluid through the vaginal cavity and being in flexible engagement with said shaft to permit relative slidable movement therebetween.

8. A uterine manipulator as set forth in claim 7, further comprising a vaginal extender mounted to said shaft of said uterine manipulator which receives said tip mount and said tip, and wherein said vaginal occluder includes a main body having a first end thereof retained between said tip mount and said vaginal extender to inhibit the passage of fluid therebetween.

9. A uterine manipulator as set forth in claim 8, wherein said vaginal occluder is fabricated of an elastomeric material.

10. A uterine manipulator as set forth in claim 8, wherein said vaginal occluder first end has an opening having a diameter smaller than the diameter of said tip mount.

11. A uterine manipulator as set forth in claim 7, including a fluid conduit fluidically connected to said occluder.

12. A uterine manipulating assembly for insertion into a vaginal cavity for use in female pelvic surgical procedures, said assembly comprising:

a uterine manipulator having an elongated shaft presenting a proximal end and a remote end, said remote end being adapted for insertion into a vaginal cavity and including a tip mount;

a tip carried on said tip mount and configured for engaging a uterus; and an elastomeric vaginal occluder having a main body comprising an annular cuff positioned in circumscribing relationship around said shaft and adapted for inflation to inhibit the passage of fluid through the vaginal cavity, said main body having a first end thereof retained between said tip and said shaft, a second end, and an outer surface, said occluder being formed by folding said second end over and sealing said second end onto said outer surface.

* * * * *